United States Patent [19]

Hubbard et al.

[11] Patent Number: 4,778,445

[45] Date of Patent: Oct. 18, 1988

[54] CENTRIFUGAL BLOOD PUMP WITH BACKFLOW DETECTION

[75] Inventors: Lloyd C. Hubbard, Minnetonka; Earl W. Clausen, Wayzata, both of Minn.

[73] Assignee: Minnesota Mining and Manufacturing Company, St. Paul, Minn.

[21] Appl. No.: 936,975

[22] Filed: Nov. 28, 1986

Related U.S. Application Data

[63] Continuation of Ser. No. 628,757, Jul. 9, 1984, abandoned.

[51] Int. Cl.$^4$ .................. A61M 1/03; F04B 49/00
[52] U.S. Cl. .................................. 604/4; 604/67; 128/691; 417/20
[58] Field of Search .......................... 604/5-7, 604/31, 50, 65-67, 118, 121, 4; 623/244, 3; 128/10, DIG. 12, DIG. 3, 691; 415/DIG. 4; 417/18-27

[56] References Cited

U.S. PATENT DOCUMENTS

| Re. 28,742 | 3/1976 | Rafferty et al. | 415/90 |
|---|---|---|---|
| 3,608,088 | 9/1971 | Dorman et al. | 3/1 |
| 3,617,151 | 11/1971 | Scroggins et al. | 417/19 |
| 3,647,324 | 3/1972 | Rafferty et al. | 417/420 |
| 3,805,768 | 4/1974 | Barefoot et al. | 128/691 |
| 3,815,582 | 6/1974 | Schuette | 128/691 |
| 3,864,055 | 2/1975 | Kletschka et al. | 415/1 |
| 3,881,483 | 4/1975 | Sausse | 604/4 |
| 3,882,861 | 5/1975 | Kettering et al. | 604/66 |
| 3,957,389 | 5/1976 | Rafferty et al. | 415/1 |
| 3,970,408 | 7/1976 | Rafferty et al. | 415/60 |
| 3,982,535 | 9/1976 | Bahrton | 604/5 |
| 4,037,984 | 7/1977 | Rafferty et al. | 415/60 |
| 4,080,966 | 3/1978 | McNally et al. | 604/50 |
| 4,108,574 | 8/1978 | Bartley et al. | 417/20 |
| 4,135,253 | 1/1979 | Reich et al. | 623/3 |
| 4,148,314 | 4/1979 | Yin | 604/5 |
| 4,180,074 | 12/1979 | Murry et al. | 604/31 |
| 4,309,993 | 1/1982 | Brown | 604/31 |
| 4,330,238 | 5/1982 | Hoffman | 417/19 |
| 4,444,546 | 4/1984 | Pazemenas | 417/18 |
| 4,447,191 | 5/1984 | Bilstad et al. | 604/6 |
| 4,468,219 | 8/1984 | George et al. | 604/67 |
| 4,541,433 | 9/1985 | Baudino | 128/691 |

FOREIGN PATENT DOCUMENTS

1807979 11/1968 Fed. Rep. of Germany ...... 604/153

OTHER PUBLICATIONS

*Journal of Thoracic & Cardiovascular Surgery*, Nov. 83, vol. 86, No. 5, "Biomedicus".

*Primary Examiner*—Stephen C. Pellegrino
*Attorney, Agent, or Firm*—Kinney & Lange

[57] ABSTRACT

A heart/lung bypass system having a centrifugal blood pump driven by a motor detects reverse flow conditions in which blood is flowing from the load to the pump outlet. An alarm control provides an alarm signal based upon a flow magnitude signal, a pump speed (rpm) signal, and a torque signal. When the pump is at a desired initial speed and an arterial flow line from the pump is unclamped, a decrease in torque requirements indicates a reverse flow condition, and an alarm is initiated. Reverse flow conditions are also indicated by an increase in rpm followed by a decrease in flow magnitude, and by a decrease in rpm coupled with an increase in flow magnitude. In addition, when the pump is running at a constant rpm, an increase in flow magnitude followed by a decrease in torque indicates a reverse flow condition, and an alarm is sounded.

9 Claims, 1 Drawing Sheet

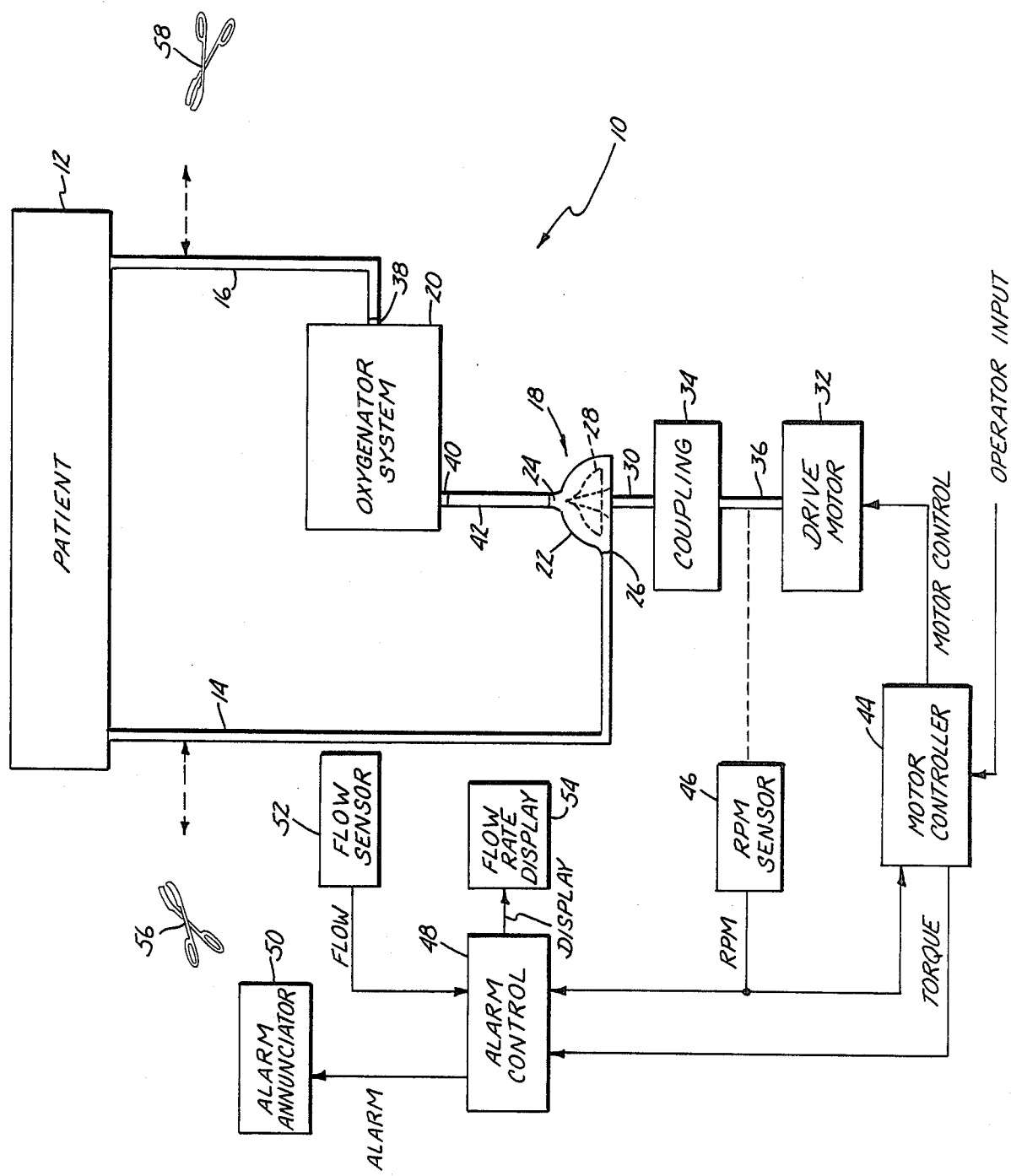

CENTRIFUGAL BLOOD PUMP WITH BACKFLOW DETECTION

This is a continuation of application Ser. No. 628,757, filed July 9, 1984 now abandoned.

BACKGROUND OF THE INVENTION

1. Field of the Invention

The present invention is related to centrifugal blood pumps, and in particular to the use of centrifugal blood pumps during open-heart surgery.

2. Description of the Prior Art

Centrifugal pumps have been used for many years to pump a wide variety of different fluid materials. In general, a centrifugal pump includes a pumping chamber with an inlet aligned with a rotational axis of the pump, an outlet adjacent the periphery of the pumping chamber, and an impeller mounted within the pumping chamber for rotation about the axis. The impeller in such pumps can be mounted on a drive shaft which extends outside the pumping chamber to a rotational drive source or the shaft can be mounted within the pumping chamber as a spindle about which the impeller rotates (rotatably driven by means other than the rotation of the shaft, such as a magnetic drive arrangement). In any case, as the impeller is rotated, it imparts centrifugal force and velocity to the fluid, thus pumping the fluid from the pump inlet to the pump outlet.

In recent years, centrifugal pumps have been used extensively for pumping blood during open heart surgery. Examples of centrifugal blood pumps are shown in the following U.S. patents: Rafferty et al U.S. Pat. No. Re. 28,742; Dorman et al U.S. Pat. No. 3,608,088; Rafferty et al U.S. Pat. No. 3,647,324; Kletschka et al U.S. Pat. No. 3,864,055; Rafferty et al U.S. Pat. No. 3,957,389; Rafferty et al U.S. Pat. No. 3,970,408; Rafferty et al U.S. Pat. No. 4,037,984; and Reich et al U.S. Pat. No. 4,135,253.

In those heart/lung bypass systems using a centrifugal pump, an arterial flow line is connected between the outlet of the centrifugal pump and an artery of the patient, and a venous flow line is connected between a vein of the patient and the inlet of the centrifugal pump. An oxygenator system is also provided at some point in the bypass system. When a bubble oxygenator is used, it is typically placed in the venous flow line between the patient and the pump. When a membrane oxygenator is used, a venous reservoir is usually placed in the venous flow line between patient and pump and the membrane oxygenator itself is placed in the arterial flow line between pump and patient.

Proper operation of the heart/lung bypass system requires that the outlet pressure of the pump exceed the blood pressure from the patient, and other pressure factors (such as the relative height of the patient and the system components) which combine to define a "load" pressure, so that flow of blood is from the outlet of the centrigual pump to the patient and from the patient back to the inlet of the pump. If the load pressure exceeds the outlet pressure of the pump, flow will be in the reverse direction, and the system will not be performing its function of replacing the heart and lungs during the open-heart surgery.

The sensing of blood flow in the heart/lung bypass system is preferably performed by a noncontacting type of flowmeter. This reduces the chance of contamination or damage to the blood by contact. In addition, since all parts of the system which contact the blood must be disposed of or resterilized after a single use, a noncontacting type flowmeter is preferable since it can be reused without resterilization.

One particularly advantageous type of noncontacting flowmeter for sensing blood flow is an ultrasonic Doppler flowmeter. While there are significant advantages (including noncontacting operation and high accuracy) provided by ultrasonic Doppler flowmeters, these types of flowmeters provide an indication only of flow magnitude, but not flow direction. An ultrasonic flowmeter, therefore, cannot distinguish between flow from the centrifugal pump to the patient and reverse flow from the patient to the centrifugal pump.

SUMMARY OF THE INVENTION

The present invention provides an indication of reverse flow in a system which includes a centrifugal pump, even though the flowmeter used to measure flow magntiude is not capable of determining direction of flow. The present invention includes an rpm sensor for sensing revolution rate of the centrifugal pump in addition to a flowmeter which senses blood flow through a flow line connected between the pump and the load.

In the present invention, changes in blood flow rate and changes in revolution rate of the centrifugal pump are monitored. An alarm signal indicating reverse flow is provided based upon the sign of flow rate change and the sign of rpm change.

In particular, an increase in rpm followed by an increase in flow rate magnitude indicates that flow is from the pump to the load. Similarly, a decrease in rpm followed by a decrease in flow rate magnitude also indicates flow from pump to load.

On the other hand, an increase in rpm followed by a decrease in flow rate magnitude, or a decrease in rpm followed by an increase in flow rate magnitude indicates reverse flow from the load to the pump. In either of these latter two conditions, the system of the present invention provides an alarm signal indicating tha reverse flow conditions exist.

In preferred embodiments of the present invention, the system also inclues means for sensing changes in torque in the drive applied to the centrifugal pump. This permits the detection of reverse flow conditions when pump rpm is constant or when flow starts from zero (such as when the arterial flow line in a heart/lung bypass system is initially unclamped).

In these preferred embodiments, a base line torque is measured while the centrifugal pump is spinning and no flow is occurring (such as when the line is clamped). When the line is unclamped, forward flow increases torque requirements above the base line torque. Reverse flow decreases torque requirements from the base line torque. The system of the present invention also provides an alarm signal indicating reverse flow conditions when flow has changed from zero and a negative change in torque occurs.

BRIEF DESCRIPTION OF THE DRAWINGS

The FIGURE shows a heart/lung bypass system of the present invention.

DETAILED DESCRIPTION OF THE PREFERRED EMBODIMENTS

Heart/lung bypass system 10 shown in the FIGURE illustrates a typical arrangement for providing life support to patient 12 during open heart surgery. System 10 includes arterial flow line 14, which is connected to an artery of the patient, venous flow line 16 which is connected to a vein of the patient, centrifugal blood pump 18, and an oxygenator system 20. Depending upon the type of oxygenator system used (bubble, membrane or other), its location in the bypass system may vary with respect to the blood pump 18. For purposes of simplifying the present discussion, oxygenator system 20 is illustrated schematically in the FIGURE and discussed as being placed in the venous flow line between patient and pump.

Centrifugal pump 18 includes housing 22, inlet 24, outlet 26, impeller 28 and drive shaft 30. Drive motor 32 provides rotary drive to drive shaft 30, and thus to impeller 28 through coupling 34. In one embodiment, coupling 34 is a magnetic type coupling, and in other embodiments is a quick connect/disconnect shaft coupling. As motor shaft 36 of drive motor 30 is rotated, coupling 34 imparts the rotary drive to pump drive shaft 30. This causes impeller 28 to rotate within housing 22, thus pumping blood from inlet 24 to outlet 26.

Arterial flow line 14 is connected between pump outlet 26 and an artery of patient 12. Venous flow line 16 is connected between a vein of pateint 12 and inlet 38 of oxygenator system 20. Outlet 40 of oxygenator system 20 is connected through interconnect flow line 42 to pump inlet 24.

During normal operation of system 10, pump 18 pumps blood from oxygenator system 20 to patient 12 through arterial flow line 14. The return blood flow path is through a venous flow line 16 to inlet 38 of oxygenator system 20. The rate of flow of blood through system 10, and the direction of flow depends upon the pump outlet pressure, and the load pressure of the load (i.e. patient 12). For proper operation, the pump outlet pressure must exceed the load pressure, so that the flow of blood is from pump outlet 26 through arterial flow line 14 to patient 12. If the pump outlet pressure is less than the load pressure, flow will be in the reverse direction from patient 12 through arterial flow line 14 to pump outlet 26. In that case, the heart/lung bypass system 10 is failing to perform properly, and an alarm must be provided.

The pump outlet pressure depends upon the rate of rotation of motor shaft 36 and pump drive shaft 30. Motor controller 44 provides a motor control signal to drive motor 32, which controls the speed of motor 32. The motor control signal is based upon an operator input signal (which selects a desired speed) and upon a feedback signal (such as the rpm signal from rpm sensor 46 which senses the rate of rotation of shaft 36).

System 10 of the present invention provides an alarm which indicates to the operator of system 10 (a perfusionist) that a reverse flow condition is present. Alarm control 48 provides an alarm signal to alarm annunciator 50 based upon a torque signal from motor controller 44, the rpm signal from rpm sensor 46, and a flow signal from flow sensor 52. In addition, alarm control 48 provides a flow rate display signal to flow rate display 54.

In preferred embodiments of the present invention, alarm control 48 is a digital electronic control, such as a microcomputer. Alarm annunciator 50 is preferably an audible or light annunciator which provides a warning alarm to the operator in response to the alarm signal from alarm control 48.

Flow sensor 52 is a noncontacting type flow sensor. In other words, the flow rate of blood through arterial flow line 14 is sensed by flow sensor 52 without contacting the blood. One advantageous type of noncontacting flowmeter used in a preferred embodiment of the present invention is an ultrasonic Doppler flowmeter.

The flow signal from flow sensor 52 provides an indication of magnitude of the flow rate of blood through arterial flow line 14. Alarm control 48 causes flow rate display 54 to display the flow rate magnitude based upon the flow signal from flow sensor 52. Flow rate display 54 is preferably a digital type display.

The flow signal from flow sensor 52, however, does not provide an indication of the direction of flow through arterial flow line 14. In order to determine the direction of flow through arterial flow line 14 at all times, alarmm control 48 uses the flow signal, the rpm signal, and the torque signal.

In one embodiment of the present invention, in which drive motor 32 is a DC motor, the motor control signal is a DC drive current. The torque signal simply represents the magnitude of the motor control signal. In other embodiments, the torque signal is derived from an error signal representing a difference between a command speed based upon the operator input signal and a feedback speed based, for example, upon the rpm signal or upon a feedback signal from windings of motor 32.

When patient 12 is first connected to heart/lung bypass system 10, clamps 56 and 58 clamp arterial and venous flow lines 14 and 16, respectively, so that no flow occurs through system 10. The operator then provides an operator input to motor controller 44 which sets the speed of drive motor 32 at a level which is estimated to generate an outlet pressure which is greater than that of patient 12. Arterial line 14 must not be unclamped until pump 18 is operating and is up to the desired speed.

While pump 18 is being driven and arterial flow line 14 is still clamped so that no flow is occurring, alarm control 48 reads and stores a base line torque value based upon the torque signal from motor control 44. When lines 14 and 16 are then unclamped, forward flow from pump outlet 26 to patient 12 through arterial line 14 will result in an increase in torque requirements. In contrast, reverse flow results in a decrease in torque requirements from the base line torque. Thus a change in the flow signal from zero together, with a decrease in torque from the base line torque value indicates a reverse flow condition. Alarm 48 provides an alarm signal to alarm annunciator 50, which warns the operator of a reverse flow condition.

Once the flow through arterial flow line 14 is non-zero; alarm control 48 continues to monitor the flow direction based upon the rpm signal from rpm sensor 48 and the flow signal from flow sensor 52. Alarm control 48 monitors changes in the rpm and flow signals, and determines the direction of blood flow in arterial flow line 14 based upon the sign of flow rate (e.g. cm$^3$/sec.) change and the sign of rpm change.

In particular, an increase in rpm followed by an increase in flow rate magnitude indicates that flow is from pump 18 to patient 12. Similarly, a decrease in rpm together with a decrease in flow rate magnitude also indicates flow from pump 18 to patient 12.

On the other hand, an increase in rpm coupled with a decrase in flow rate magnitude, or a decrase in rpm coupled with an increase in flow rate magnitude indicates that the blood flow is from patient 12 to pump 18 through arterial flow line. Whenever alarm control 48 determines a reverse flow condition based upon the rpm and flow signals, it provides an alarm to alarm annunciator 50.

In a preferred embodiment of the present invention, alarm control 48 also provides an alarm signal if the rpm of the pump is below a predetermined minimum value, so that the perfusionist is warned not to unclamp flow lines 14 and 16 when pump 18 is not up to speed. This, in turn, ensures that a change in torque from the base line torque value will occur in the event of reverse flow when arterial flow line 14 is unclamped.

Although unlikely, backflow is possible when a patient is being perfused during surgery and the pump 18 is operated at a constant rpm. During this type of perfusion, the patient's vascular resistance (blood pressure) will vary from time to time. This will, in turn, cause variations in flow and torque demands at a constant rpm. The alarm control 48 is programmed to analyze such conditions to avoid false backflow alarms.

Table 1 illustrates the bases from which our alarm control 48 determines whether to provide an alarm signal.

TABLE 1

| FLOW CHANGE | TORQUE CHANGE | RPM CHANGE | RPM OVER MIN | ALARM? |
|---|---|---|---|---|
| DC | DC | DC | NO | YES |
| + | + | 0 | YES | NO |
| + | − | 0 | DC | YES |
| + | DC | + | YES | NO |
| + | DC | − | DC | YES |
| − | DC | − | YES | NO |
| − | DC | + | DC | YES |
| − | − | 0 | YES | NO |
| − | + | 0 | DC | YES |

TABLE I KEY:
0 = none
+ = increase
− = decrease
DC = Don't Care

With system 10 of the present invention, a reliable indication of reverse flow conditions is provided without requiring a flow sensor which contacts the blood itself. This minimizes the likelihood of damage or contamination of the blood.

Although the present invention has been described with reference to preferred embodiments, workers skilled in the art will recognize that changes may be made in form and detail without departing from the spirit and scope of the invention.

What is claimed is:

1. A heart/lung apparatus for connection to a patient during heart surgery comprising:
   a centrifugal pump having a pump inlet, a pump outlet, a housing and an impeller which rotates within the housing;
   an arterial flow line connected between the pump outlet and an artery of the patient;
   a venous flow line connected between the pump inlet and a vein of the patient;
   non-directional flow sensing means for sensing blood flow rate magnitude in the arterial flow lines and providing a flow signal representative of the blood flow rate magnitude;
   means for sensing revolution rate of the impeller of the centrifugal pump and providing a revolution rate signal representative of revolution rate magnitude;
   means responsive to changes in the flow signal and the revolution rate signal with time for providing an alarm signal (a) when an increase in the revolution rate magnitude is followed by a decrease in the flow rate magnitude, and (b) when a decrease in the revolution rate magnitude is followed by an increase in the flow rate magnitude.

2. The apparatus of claim 1 and further comprising:
   means for providing a torque signal indicative of torque demand magnitude of the centrifugal pump;
   means for storing a base line torque value based upon magnitude of the torque signal when the pump is running at a fixed rpm and the flow rate magnitude is constant; and
   means responsive to the flow signal and the torque signal for providing an alarm signal when the flow rate magnitude increases and the torque demand magnitude decreases from the base line torque value.

3. The apparatus of claim 2 and further compirising:
   means responsive to the flow signal and the torque signal for providing an alarm signal when the flow rate magnitude decreases and the torque demand magnitude increases from the base line torque value.

4. The apparatus of claim 1 and further comprising:
   means responsive to the revolution rate signal for providing an alarm signal when the revolution rate magnitude is less than a predetermined value.

5. The apparatus of claim 1 wherein the means for sensing blood flow comprises an ultrasonic flow sensor.

6. A pumping apparatus for pumping liquid to a load, the system comprising:
   a centrifugal pump having a pump inlet, a pump outlet, a housing and an impeller which rotates within the housing;
   a reservoir of the liquid connected to the pump inlet;
   a flow line connecting the pump outlet to the load;
   non-directional flow sensing means for providing a flow signal representative of sensed flow rate magnitude in the flow line;
   means for providing a speed signal representative of sensed speed magnitude of the impeller of the pump; and
   means responsive to the flow signal representative of the sensed flow rate in the flow line and the speed signal representative of the sensed speed of the pump for providing an alarm signal (a) when the flow rate magnitude increases following a decrease in magnitude in the speed, and (b) when the flow rate magnitude decreases following an increase in the speed magnitude.

7. The apparatus of claim 6 and further comprising:
   means for providing a torque signal indicative of torque demand magnitude of the centrifugal pump;
   means for storing a base line torque value based upon the torque signal when the pump is running and the flow rate magnitude is constant; and
   means responsive to the flow signal and the torque signal for providing an alarm signal when the sensed flow rate magnitude increases and the torque demand magnitude decreases from the base line torque value.

8. The apparatus of claim 7 and further comprising:
   means responsive to the flow signal and the torque signal for providing an alarm signal when the sensed flow rate magnitude decreases and the torque demand magnitude increases from the base line torque value.

9. The apparatus of claim 6 and further comprising:
   means responsive to the speed signal for providing an alarm signal when the sensed speed magnitude is less than a predetermined value.

* * * * *